United States Patent
Dodd et al.

(12) 
(10) Patent No.: US 6,610,697 B1
(45) Date of Patent: Aug. 26, 2003

(54) SUBSTITUTED 2-ARYL-3-(HETEROARYL)-IMIDAZO[1,2-A]PYRIMIDINES, AND RELATED PHARMACEUTICAL COMPOSITIONS AND METHODS

(75) Inventors: John H. Dodd, Pittstown, NJ (US); James R. Henry, Indianapolis, IN (US); Kenneth C. Rupert, South Orange, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/698,448

(22) Filed: Oct. 27, 2000

Related U.S. Application Data
(60) Provisional application No. 60/164,700, filed on Nov. 10, 1999.

(51) Int. Cl.[7] ............... C07D 487/04; A61K 31/519; A61P 19/02
(52) U.S. Cl. ............ 514/259.1; 544/281; 544/60; 544/111; 540/467; 540/470; 540/488; 540/492; 514/227.8; 514/231.5; 514/211.01; 514/211.15; 514/212.02
(58) Field of Search ............... 544/281; 514/258, 514/259.1

(56) References Cited

U.S. PATENT DOCUMENTS
2,785,133 A * 3/1957 Craig et al. ............... 252/152

FOREIGN PATENT DOCUMENTS

| | | | |
|---|---|---|---|
| EP | 0403251 | A2 | 6/1990 |
| WO | WO90/15534 | A1 | 12/1990 |
| WO | WO91/00092 | A1 | 1/1991 |
| WO | WO91/19497 | A1 | 12/1991 |
| WO | WO93/14081 | A1 | 7/1993 |
| WO | WO98/07425 | A1 | 2/1998 |
| WO | WO99/01449 | A1 | 1/1999 |

OTHER PUBLICATIONS
Dinarello et al., Curr. Opin. Immunol., 1991, 3: 941–8.
Boehm et al., J. Med. Chem., 1996, 39:3929–37.
Badger, et al, J. Pharm. Exp. Therap., 1996, 279:1453–61.
Elliot et al., Arthritis Rheum. 1993, 36: 1681– 90.
Griswold et al., Pharm. Commun., 1996, 7:323–9.

* cited by examiner

*Primary Examiner*—Mark L. Berch
*Assistant Examiner*—Venkataraman Balasubramanian
(74) *Attorney, Agent, or Firm*—Joseph S. Kentoffio

(57) ABSTRACT

This invention relates to a series of imidazopyrimidines of Formula I,

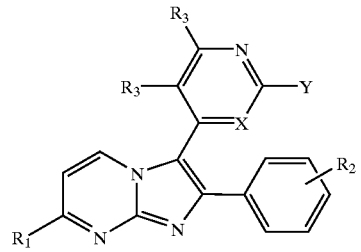

Formula I and pharmaceutical compositions containing them. The compounds of the invention inhibit the production of a number of inflammatory cytokines and are useful in the treatment and prevention of diseases associated with the overproduction thereof.

36 Claims, No Drawings

SUBSTITUTED 2-ARYL-3-(HETEROARYL)-IMIDAZO[1,2-A]PYRIMIDINES, AND RELATED PHARMACEUTICAL COMPOSITIONS AND METHODS

This application claims the benefit under 35 U.S.C. §119(e) of prior application Ser. No. 60/164,700, filed Nov. 10, 1999.

FIELD OF THE INVENTION

This invention relates to a series of substituted imidazopyrimidines and pharmaceutical compositions containing them. The compounds of the invention inhibit the production of a number of inflammatory cytokines, particularly TNF-α and IL-1β. Compounds of this invention are useful in the treatment of diseases mediated by p38, such as rheumatoid arthritis, inflammatory bowel disease, septic shock, osteoporosis, osteoarthritis, neurodegenerative disorders, and AIDS-related diseases.

BACKGROUND OF THE INVENTION

The inflammatory cytokines TNF-α and IL-1β play an important role in a number of inflammatory diseases such as rheumatoid arthritis (Dinarello et al., Curr. Opin. Immunol., 1991, 3: 941–8). Arthritis is an inflammatory disease which affects millions of people and can strike at any joint in the human body. Its symptoms range from mild pain and inflammation in affected joints, to severe and debilitating pain and inflammation. Although the disease is associated mainly with aging adults, it is not restricted to adults.

The most common arthritis therapy involves the use of nonsteroidal anti-inflammatory drugs ("NSAID's") to alleviate the symptoms. However, despite the widespread use of NSAID's, many individuals cannot tolerate the doses necessary to treat the disease over a prolonged period of time. In addition, NSAID's merely treat the symptoms of the disease without affecting the underlying cause. Other drugs such as methotrexate, D-pencillamine, gold salts, and Frednione are often used when patients fail to respond to NSAID's. These drugs also have significant toxicities and their mechanisms of action remain unknown.

Receptor antagonists to IL-1β and monoclonal antibodies to TNF-α have been shown to reduce symptoms of rheumatoid arthritis in small-scale human clinical trials. In addition to protein-based therapies, there are small molecule agents which inhibit the production of these cytokines and have demonstrated activity in animal arthritis models (Boehm et al., J. Med. Chem., 1996, 39:3929–37). Of these small molecule agents, SB 203580 has proven effective in reducing the production of TNF-α and IL-1 in LPS-stimulated human monocyte cell lines with $IC_{50}$ values of 50 to 100 nM (Adams et al., WO 93/14081, Jul. 23, 1993). In addition to this in vitro test, SB 203580 inhibits the production of the inflammatory cytokines in rats and mice at $IC_{50}$ values of 15 to 25 mg/kg (Badger,et al, J. Pharm. Exp. Therap., 1996, 279:1453–61). Although human data are currently unavailable for SB 203580, monoclonal antibodies to TNF-α have proven efficacious in the treatment of rheumatoid arthritis (Elliot et al., Arthritis Rheum. 1993, 36: 1681–90). Due to SB 203580's oral activity and potency in animal models, researchers have suggested that a compound with this profile has potential as a viable treatment for rheumatoid arthritis (Badger et al., J. Pharm. Exp. Therap., 1996, 279:1453–61).

SB 203580 and other small molecule agents reduce the production of inflammatory cytokines by inhibiting the activity of a serine/threonine kinase p38, which sometimes is referred to as CSBP, at an $IC_{50}$ of 200 nM (Griswold et al., Pharm. Commun., 1996, 7:323–9). Although the precise role of this kinase is unknown, it has been implicated in both the production of TNF and the signaling responses associated with the TNF-α receptor.

WO 91/00092 discloses a method of inhibiting the production of interleukin-1 by monocytes and/or macrophages in humans by administering a diaryl-substituted imidazole fused to a second heterocyclic ring containing a nitrogen bridgehead atom, wherein the second ring may also contain sulfur, oxygen or an additional nitrogen atom, and may contain additional unsaturation.

WO 90/15534 and EP 0403251 disclose treatments of humans afflicted with a T Cell Viral (TIV) infection which comprises administering an effective amount of a monokine activity-reducing agent.

WO 91/19497 discloses a diaryl-substituted imidazole compound useful in dual inhibition of 5-lipoxygenase pathway-mediated diseases and cyclooxygenase pathway-mediated diseases. This compound is fused to a second unsaturated 5 or 6 membered heterocyclic ring containing a nitrogen bridgehead atom, wherein the second 5 membered ring also contains a sulfur or oxygen atom and the 6 membered ring may also contain an additional nitrogen atom.

Despite these known compounds and methods, there remains a need in the art for improved methods of reducing inflammatory cytokine production through inhibiting serine/threonine kinase p38 activity, and for related methods of treating and preventing arthritis and other inflammatory disorders.

SUMMARY OF THE INVENTION

This invention provides novel compounds which inhibit the in vitro activity of p38 in the nanomolar range as well as methods for making same. In addition, the compounds of the present invention inhibit the in vitro secretion of TNF-α and IL-1β in the nanomolar range. Animal models demonstrate the inhibition of LPS-induced TNF-α production. Demonstrated to have these biological activities by in vitro and in vivo assays described hereinafter are the compounds of the present invention as shown in Formula I:

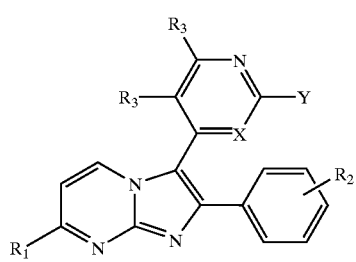

Formula I

This invention also provides a pharmaceutical composition comprising the instant compound and a pharmaceutically acceptable carrier, as well as related synthetic methods.

This invention further provides a method of treating a subject suffering from a condition whose alleviation is mediated by the reduction of inflammatory cytokines whose actions contribute to the condition, which method comprises administering to the subject a therapeutically effective dose of the instant pharmaceutical composition.

This invention still further provides a method of inhibiting in a subject the onset of a condition whose alleviation is mediated by the reduction of inflammatory cytokines whose actions contribute to the condition, which method comprises administering to the subject a prophylactically effective dose of the instant pharmaceutical composition.

DETAILED DESCRIPTION OF THE INVENTION

This invention provides a compound of Formula I,

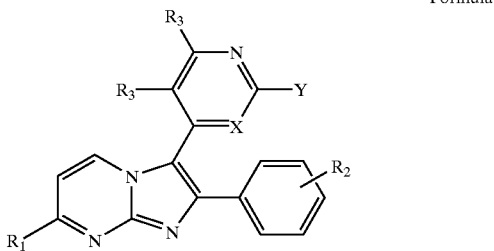

Formula I or a pharmaceutically acceptable salt thereof, wherein (a) $R_1$ is selected from $NH_2$, $C_{1-5}$alkylamino, $diC_{1-5}$alkylamino, hydroxy, $C_{1-5}$alkoxy, phenylmethylamino, heterocyclylmethyl, $C_{1-5}$alkylcarbonylamino, and substituted phenylcarbonylamino, wherein said phenylmethylamino and heterocyclylmethyl may be substituted on its phenyl moiety by one or more members selected from the group consisting of halogen, $C_{1-5}$alkyl, $C_{1-5}$alkoxy, aryl$C_{1-3}$alkylamino, R'R"NCH=N— and OR'", the R', R", and R"' being independently selected from H, $C_{1-5}$alkyl, phenylmethyl, substituted phenylmethyl, α-alkyl-phenylmethyl, substituted α-alkyl-phenylmethyl, heterocyclylmethyl, and substituted heterocyclylmethyl;

(b) Y is selected from the group consisting of H, halogen, heterocycle, $OR_4$, $SR_4$, $NR_4$, and $NR_4R_5$, wherein $R_4$ and $R_5$ are independently selected from H, heterocyclyl, $C_{3-5}$carbocycle, phenyl, α-alkyl-phenyl$C_{1-5}$alkyl, straight or branched alkyl optionally substituted with R, NR, N(R)$_2$, $C_{3-5}$carbocycle, phenyl or substituted phenyl, wherein (i) R is H, halogen, $C_{1-5}$alkyl, phenyl methyl, substituted phenyl methyl, $SO_2Ph$, pyridyl, or pyridyl methyl, and (ii) said phenyl, heterocyclyl, and α-alkyl-phenyl$C_{1-5}$alkyl may be substituted by one or more members selected from the group consisting of halogen, $C_{1-5}$alkyl, $C_{1-5}$alkoxy, aryl$C_{1-3}$alkylamino, phenyl methyl, substituted phenyl methyl, R'R"NCH=N— and OR'" as defined in (a) hereof;

(c) $R_2$ is one to five members independently selected from the group consisting of halogen, trifluoromethyl, —NCH$_2$PH, $C_{1-5}$alkyl, and $C_{1-5}$alkoxy;

(d) $R_3$ is H or, taken together, an aromatic ring; and (e) X is N or CH.

In one embodiment of the instant compound, $R_1$ is $NH_2$. In another embodiment, $R_2$ is a member selected from the group consisting of halogen, trifluoromethyl, —NCH$_2$PH, and $C_{1-5}$alkoxy. In yet another embodiment, Y is $NR_4$ and $R_4$ is phenylmethyl. In still another embodiment, X is CH.

Unless specified otherwise, the term "alkyl" refers to a straight, branched or cyclic substituent consisting solely of carbon and H with no unsaturation. The term "alkoxy" refers to O-alkyl where alkyl is as defined supra. The term "aromatic ring" refers to a 5- to 6-membered ring containing a 6-electron delocalized conjugated pi bonding system such as phenyl, furanyl, and pyrrolyl. The term "aryl" includes mono and fused aromatic rings such as phenyl, naphthyl, diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. The term "halo" means fluoro, chloro, bromo and iodo. The symbol "Ph" refers to phenyl. The term "heterocyclyl", "heterocycle" or "heterocyclic residue" represents a single or fused ring having at least one atom other than carbon as ring member, e.g. pyridine, pyrimidine, oxazoline, pyrrole, imidazole, morpholine, furan, indole, benzofuran, pyrazole, pyrrolidine, piperidine, and benzimidazole.

Substituted heterocyclylmethyl and substituted phenylmethyl have substituents such as halogen, $C_{1-5}$alkyl, $C_{1-5}$alkoxy, aryl$C_{1-3}$alkylamino, R'R"NCH=N—, and OR'" wherein R', R", and R"' are independently selected from H, $C_{1-5}$alkyl, phenylmethyl, substituted phenylmethyl, α-alkyl-phenylmethyl and substituted α-alkyl-phenylmethyl, heterocyclylmethyl, and substituted heterocyclylmethyl.

The term "FCS" represents fetal calf serum, "TCA" represents trichloroacetic acid, and "RPMI" represents the medium from the Roswell Park Memorial Inst. (Sigma cat #R0833). "Independently" means that when there is more than one substituent, the substituents may be different. "DME" refers to ethylene glycoldimethyl. The term "NaH-MDS" refers to sodium hexamethyldisilazide.

The phrase "pharmaceutically acceptable salt" denotes salts of the free base which possess the desired pharmacological activity of the free base and which are neither biologically nor otherwise undesirable. These salts may be derived from inorganic or organic acids. Examples of inorganic acids are hydrochloric acid, hydrobromic acid, hydroiodic acid, perchloric acid, nitric acid, sulfuric acid and phosphoric acid. Examples of organic acids are acetic acid, propionic acid, glycolic acid, lactic acid, pyruvic acid, malonic acid, succinic acid, malic acid, maleic acid, maieic acid, fumaric acid, tartaric acid, citric acid, benzoic acid, cinnamic acid, mandelic acid, oxalic acid, pamoic acid, saccharic acid, methanesulfonic acid, ethanesulfonic acid, p-toluenesulfonic acid, methyl sulfonic acid, salicyclic acid, hydroethanesulfonic acid, benzenesulfonic acid, 2-naphthalenesulfonic acid, p-toluenesulfonic acid, cyclohexanesulfamic acid and the like.

Where the compounds according to this invention have one or more stereogenic centers, it is to be understood that all possible optical isomers, antipodes, enantiomers, and diastereomers resulting from additional stereogenic centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography in a Pirkle-type column.

The following compounds are exemplary of the present invention:

Compound 1: 2-(4-fluorophenyl)-3-(4-pyridinyl)-imidazo[1,2-a]pyrimidin-7-amine;

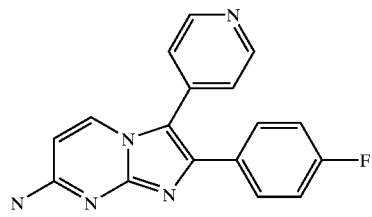
Compound 1

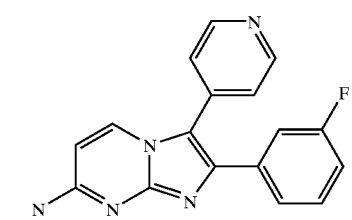
Compound 2

Compound 2: 2-(3-fluorophenyl)-3-(4-pyridinyl)-imidazo[1,2-a]pyrimidin-7-amine;

Compound 3: 2-(4-fluorophenyl)-3-(4-quinolinyl)-imidazo[1,2-a]pyrimidin-7-amine;

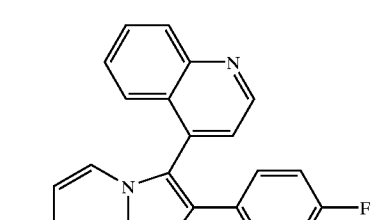
Compound 3

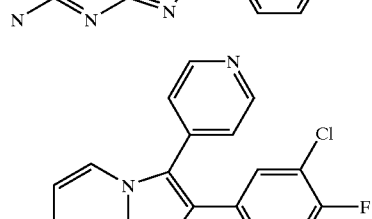
Compound 4

Compound 4: 2-(3-chloro-4-fluorophenyl)-3-(4-pyridinyl)-imidazo[1,2-a]pyrimidin-7-amine;

Compound 5: 2-phenyl-3-(4-pyridinyl)-imidazo[1,2-a]pyrimidin-7-amine;

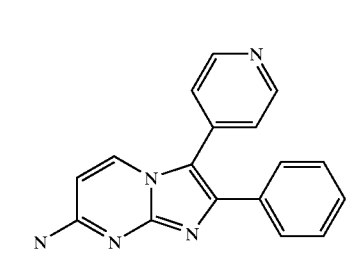
Compound 5

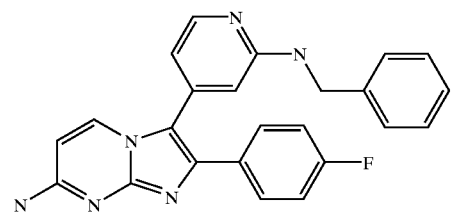
Compound 6

Compound 6: 2-(4-fluorophenyl)-3-[2-[(phenylmethyl)amino]4-pyridinyl]-imidazo[1,2-a]pyrimidin-7-amine;

Compound 7: 3-(4-pyridinyl)-2-[3-(trifluoromethyl)phenyl]-imidazo[1,2-a]pyrimidin-7-amine;

Compound 7

Compound 8

Compound 8: 3-[2-[(phenylmethyl)amino]4-pyridinyl]-2-[3-(trifluoromethyl)phenyl]-imidazo[1,2-a]pyrimidin-7-amine;

Compound 9: 3-[2-[[(1S)-1-Phenylethyl]amino]4-pyrimidinyl]-2-[3-(trifluoromethyl)phenyl]imidazo[1,2-a]pyrimidin-7-amine;

Compound 9

Compound 10

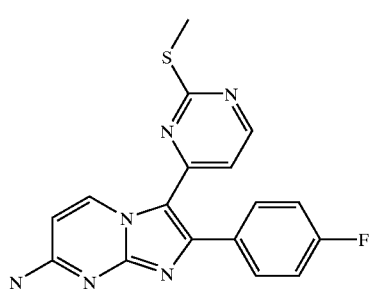

Compound 10: 2-(4-Fluorophenyl)-3-[2-(methylthio)-4-pyrimidinyl]imidazo[1,2-a]pyrimidin-7-amine;

Compound 11: 3-[2-(Methylthio)-4-pyrimidinyl]-2-[3-(trifluoromethyl)phenyl]imidazo[1,2-a]pyrimidin-7-amine;

Compound 11

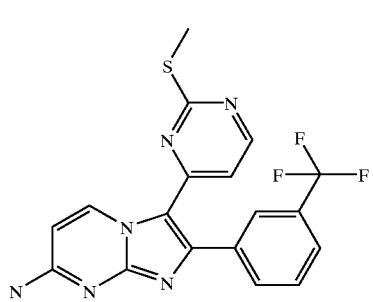

Compound 12

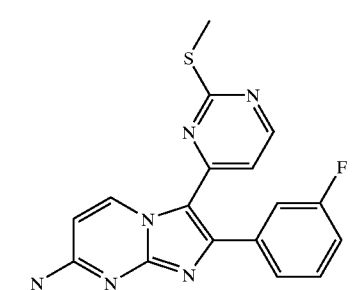

Compound 12: 2-(3-Fluorophenyl)-3-[2-(methylthio)-4-pyrimidinyl]imidazo[1,2-a]pyrimidin-7-amine;

Compound 13: 3-(4-Pyrimidinyl)-2-[3-(trifluoromethyl)phenyl]imidazo[1,2-a]pyrimidin-7-amine;

Compound 13

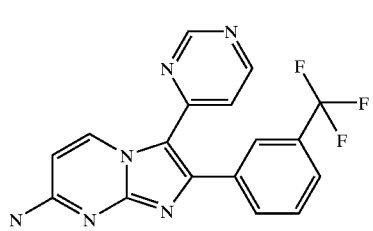

Compound 14

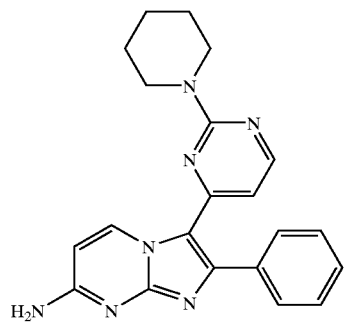

Compound 14: 2-Phenyl-3-[2-(1-piperidinyl)-4-pyrimidinyl]imidazo[1,2-a]pyrimidin-7-amine;

Compound 15: 3-[2-(Methylthio)-4-pyrimidinyl]-2-phenylimidazo[1,2-a]pyrimidin-7-amine;

Compound 15

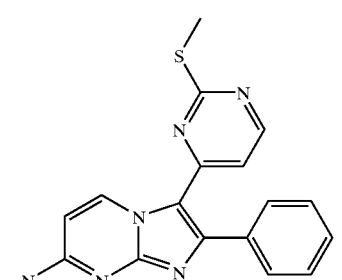

Compound 16

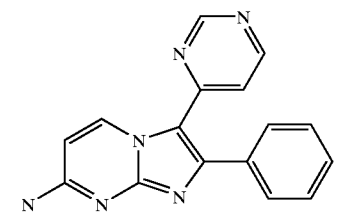

Compound 16: 2-Phenyl-3-(4-pyrimidinyl)imidazo[1,2-a]pyrimidin-7-amine;

Compound 17: 3-[2-(Methylsulfonyl)-4-pyrimidinyl]-2-phenylimidazo[1,2-a]pyrimidin-7-amine;

Compound 17

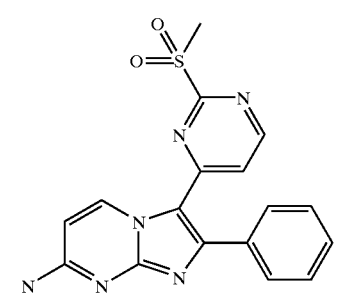

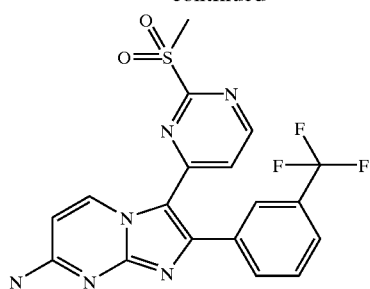

Compound 18: 3-[2-(Methylsulfonyl)-4-pyrimidinyl]-2-[3-(trifluoromethyl)phenyl]imidazo[1,2-a]pyrimidin-7-amine;

Compound 19: 2-Phenyl-3-[2-[[(1S)-1 -phenylethyl]amino]4-pyrimidinyl]imidazo[1,2-a]pyrimidin-7-amine;

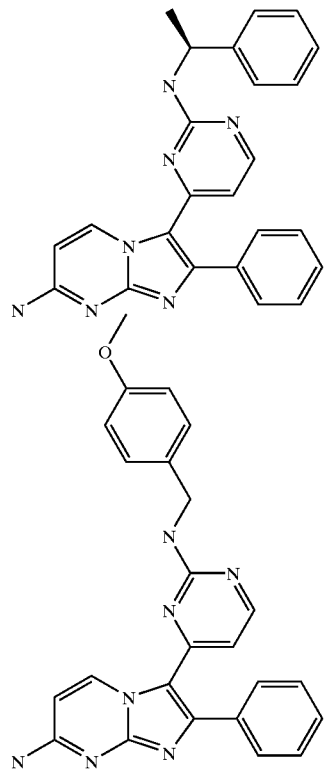

Compound 20: 3-[[[(4-Methoxyphenyl)methyl]amino]-4-pyrimidinyl]-2-phenylimidazo[1,2-a]pyrimidin-7-amine;

Compound 21: 2-(4-Fluorophenyl)-3-[3-[[(1S)-1-phenylethyl]amino]-4-pyridinyl]imidazo[1,2-a]pyrimidin-7-amine;

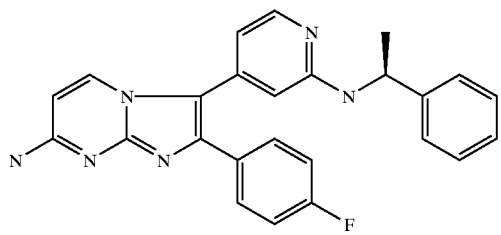

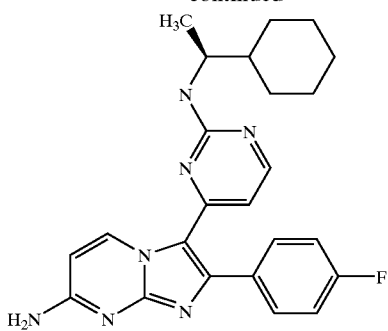

Compound 22: 3-[2-[[(1S)-1-Cyclohexylethyl]amino]-4-pyrimidinyl]-2-(4-fluorophenyl)imidazo[1,2-a]pyrimidin-7-amine;

Compound 23: 3-(2-Methoxy-4-pyrimidinyl)-2-phenylimidazo[1,2-a]pyrimidin-7-amine;

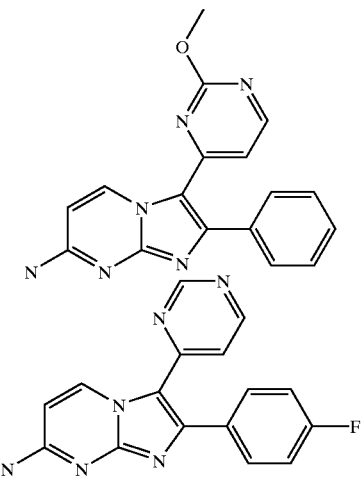

Compound 24: 2-(4-Fluorophenyl)-3-(4-pyrimidinyl)imidazo[1,2-a]pyrimidin-7-amine;

Compound 25: 2-(3-Chlorophenyl)-3-(4-pyridinyl)imidazo[1,2-a]pyrimidin-7-amine;

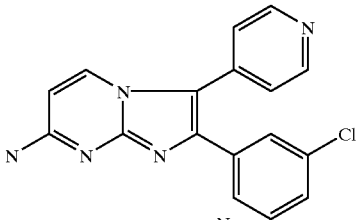

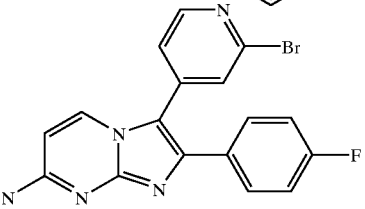

Compound 26: 3-(2-Bromo-4-pyridinyl)-2-(4-fluorophenyl)imidazo[1,2-a]pyrimidin-7-amine; and Compound 27: 3-(2-Bromo-4-pyridinyl)-2-[3-(trifluoromethyl)phenyl]imidazo[1,2-a]pyrimidin-7-amine.

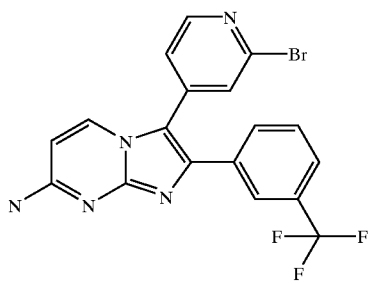

Compound 27

This invention also provides a pharmaceutical composition comprising the instant compound and a pharmaceutically acceptable carrier.

Pharmaceutical compositions containing the compound of the present invention as the active ingredient in intimate admixture with a pharmaceutical carrier can be prepared according to conventional pharmaceutical techniques. The carrier may take a wide variety of forms depending on the form of preparation desired for administration, such as topical administration and systemic administration including, but not limited to, intravenous infusion, oral, nasal or parenteral. In preparing the compositions in oral dosage form, any of the usual pharmaceutical carriers may be employed, such as water, glycerol, glycols, oils, alcohols, flavoring agents, preservatives, coloring agents, syrup and the like in the case of oral liquid preparations (for example, suspensions, elixirs and solutions); or carriers such as starches, sugars, methyl cellulose, magnesium sterate, dicalcium phosphate, mannitol and the like in the case of oral solid preparations (for example, powders, capsules and tablets). All excipients may be mixed as needed with disintegrants, diluents, granulating agents, lubricants, binders and the like using conventional techniques known to those skilled in the art of preparing dosage forms.

The preferred route of administration is oral administration. Because of their ease in administration, tablets and capsules represent an advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

As used in this invention, the term "cytokine" refers to the proteins TNF-α and IL-1β. Cytokine-related disorders are diseases of humans and other mammals where the overproduction of cytokines causes the symptoms of the disease. The overproduction of the cytokines TNF-α and IL-1β has been linked to a number of diseases.

The compounds of the present invention inhibit the production of TNF-α and IL-1β. Thus, this invention further provides a method of treating a subject suffering from a condition whose alleviation is mediated by the reduction of inflammatory cytokines whose actions contribute to the condition, which method comprises administering to the subject a therapeutically effective dose of the instant pharmaceutical composition. As used herein, the term "subject" includes, without limitation, any animal or artificially modified animal. In the preferred embodiment, the subject is a human.

This invention still further provides a method of inhibiting in a subject the onset of a condition whose alleviation is mediated by the reduction of inflammatory cytokines whose actions contribute to the condition, which method comprises administering to the subject a prophylactically effective dose of the instant pharmaceutical composition.

In one embodiment, the condition is selected from the group consisting of arthritis, inflammatory bowel disease, septic shock, osteoporosis, osteoarthritis, neuropathic pain, HIV replication, HIV dementia, viral myocarditis, insulin-dependent diabetes, non-insulin dependent diabetes, periodontal disease, restenosis, alopecia areta, T-cell depletion in HIV infection or AIDS, psoriasis, acute pancreatitis, allograft rejection, allergic inflammation in the lung, atherosclerosis, multiple sclerosis, cachexia, Alzheimer's disease, stroke, Crohn's disease, ischemia, congestive heart failure, pulmonary fibrosis, hepatitis, glioblastoma, Guillain-Barre Syndrome, and systemic lupus erythematosus. In the preferred embodiment, the condition is rheumatoid arthritis.

As used herein, "treating" a disorder means eliminating or otherwise ameliorating the cause and/or effects thereof. "Inhibiting" the onset of a disorder means preventing, delaying or reducing the likelihood of such onset. Likewise, "therapeutically effective" and "prophylactically effective" doses are doses that permit the treatment and inhibition, respectively, of a disorder. Methods are known in the art for determining therapeutically and prophylactically effective doses for the instant pharmaceutical composition. The effective dose for administering the pharmaceutical composition to a human, for example, can be determined mathematically from the results of animal studies.

In one embodiment, oral doses of the instant compounds range from about 0.05 to about 100 mg/kg, daily. In another embodiment, oral doses range from about 0.05 to about 50 mg/kg daily, and in a further embodiment, from about 0.05 to about 20 mg/kg daily. Infusion doses can range, for example, from about 1.0 to $1.0 \times 10_4$ μg/kg/min of instant compound, admixed with a pharmaceutical carrier over a period ranging from several minutes to several days. For topical administration, the instant compound can be mixed with a pharmaceutical carrier at a concentration of, for example, about 0.1 to about 10% of drug to vehicle.

Finally, this invention provides processes for preparing the instant compounds. These compounds can be prepared as shown below from readily available starting materials and/or intermediates following processes well known in the art.

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

EXPERIMENTAL DETAILS

A. Schemes and Syntheses

Compounds of Formula I in which $R_1$ is $NH_2$, and $R_3$ and Y are H may be prepared by Scheme I. A starting compound of type 1a, such as 4-methyl pyridine or 4-methyl quinoline, may be stirred with a benzoic ester of type 1b and two equivalents of a suitable hindered base, such as sodium hexamethyldisiiazide in a suitable solvent such as THF at room temperature to give the enolate of 1c which is then brominated to type 1d. An intermediate of type 1d may be further reacted with 2,6-diaminopyrimidine to give a compound of Formula I in which $R_1$ is $NH_2$ and Y is H.

SCHEME I
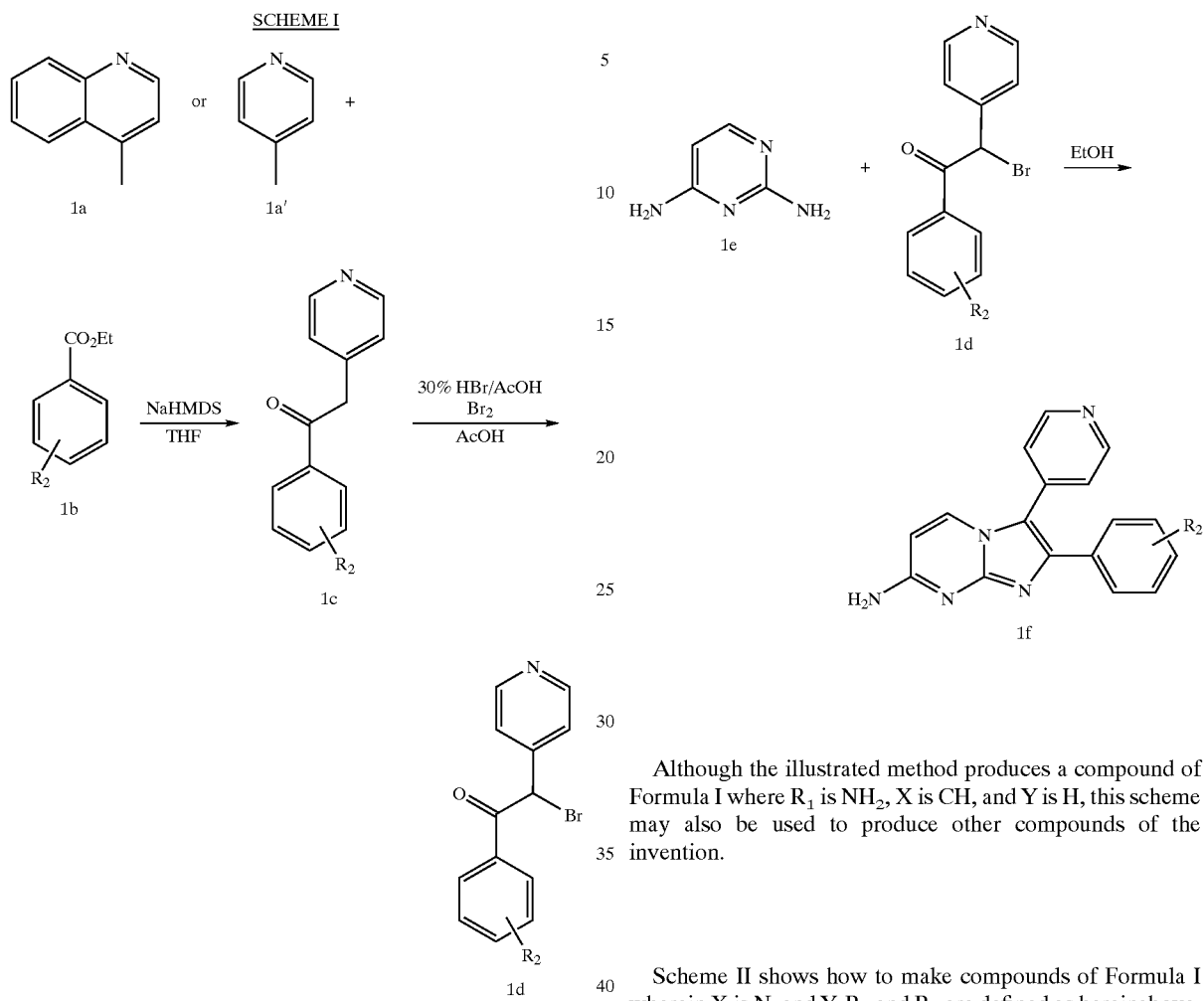
Although the illustrated method produces a compound of Formula I where $R_1$ is $NH_2$, X is CH, and Y is H, this scheme may also be used to produce other compounds of the invention.
Scheme II shows how to make compounds of Formula I wherein X is N, and Y, $R_2$ and $R_3$ are defined as hereinabove.
SCHEME II
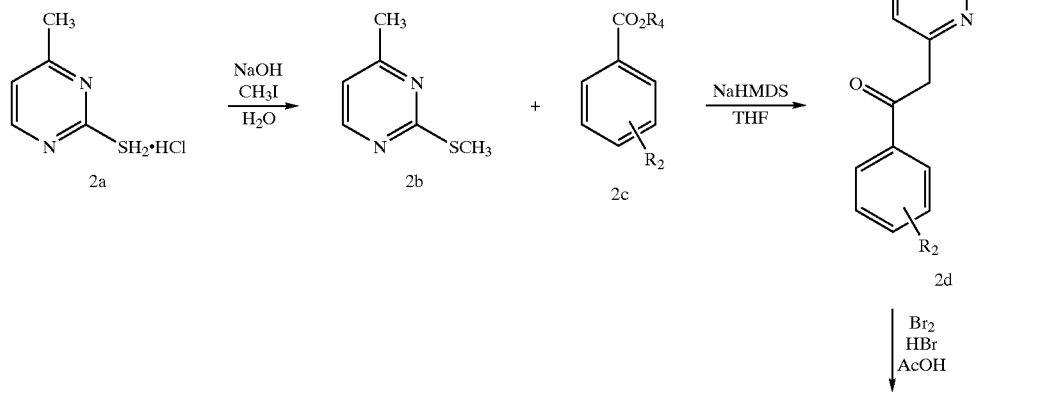

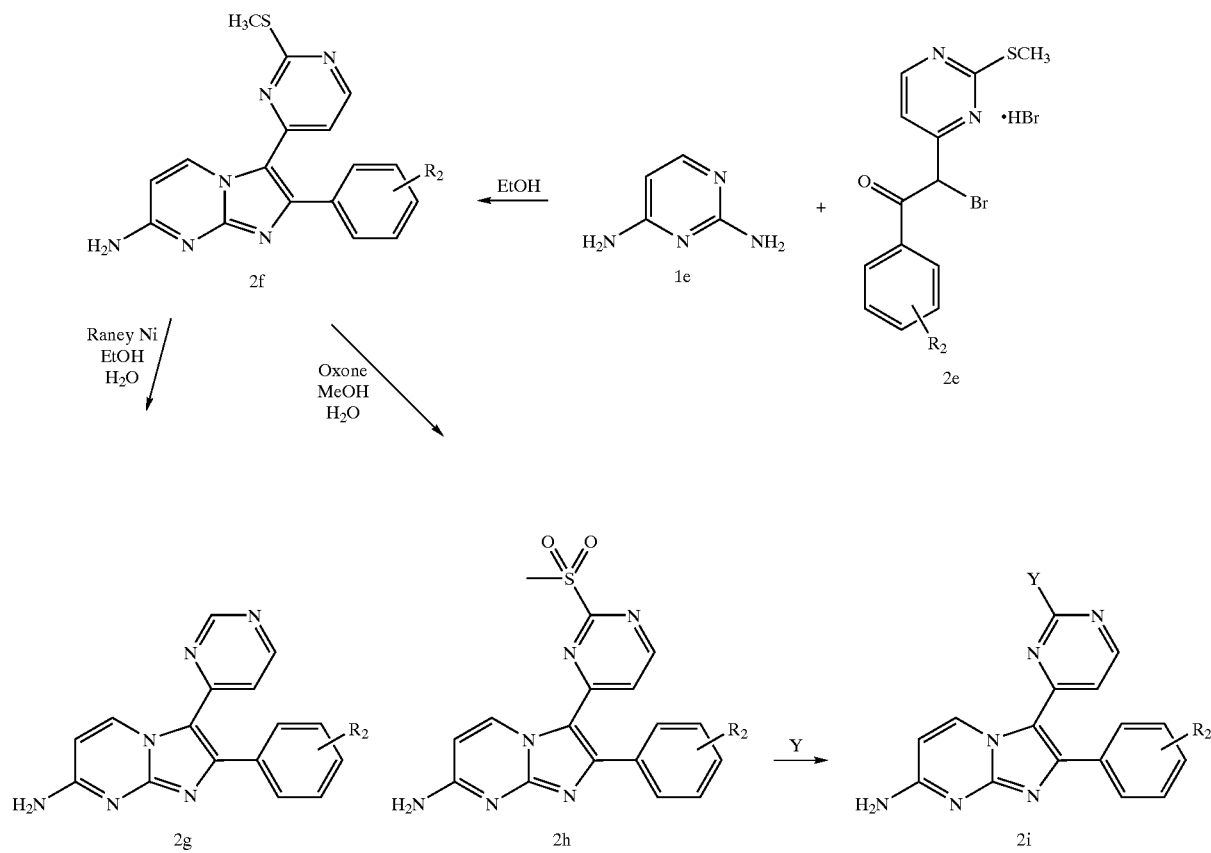
Scheme II shows how to make compounds of Formula I wherein X is CH, Z' is F, Cl or Br, and Y, $R_2$ and $R_3$ are as defined hereinabove.
SCHEME III
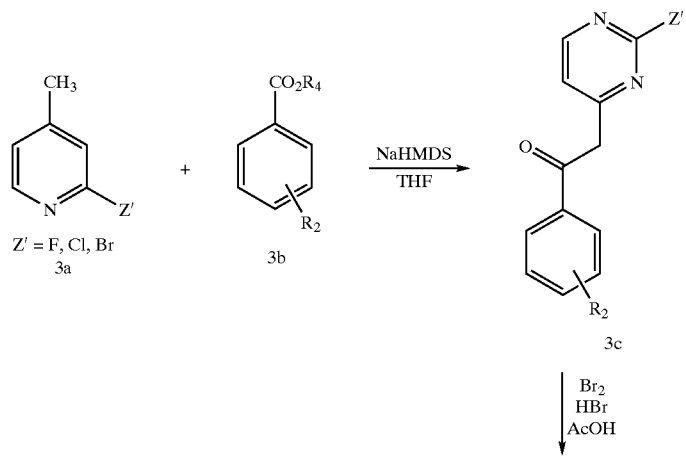

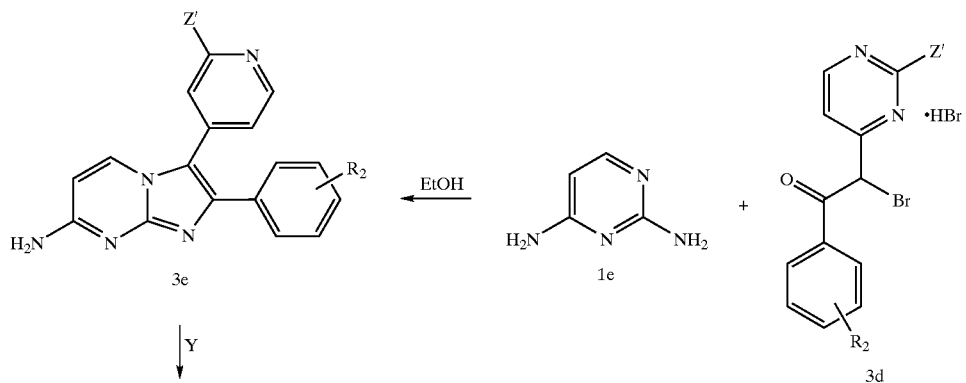
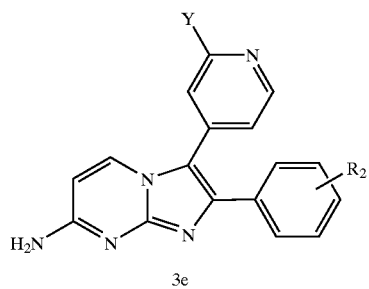
Scheme IV shows how to make compounds of Formula I wherein X is CH, Y is NR$_4$ and R$_4$ is defined as hereinabove.
SCHEME IV
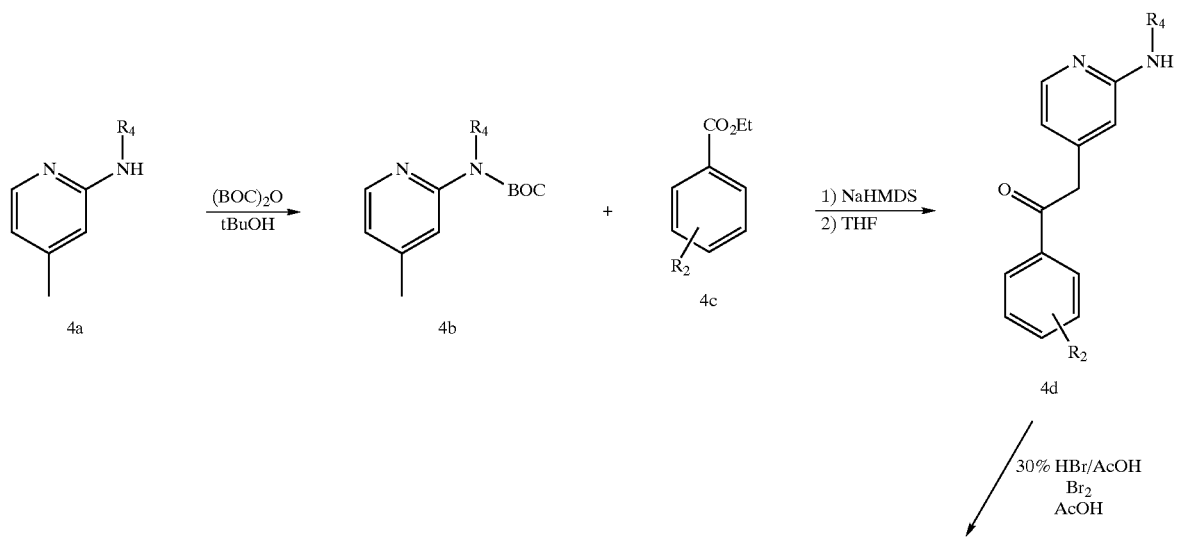

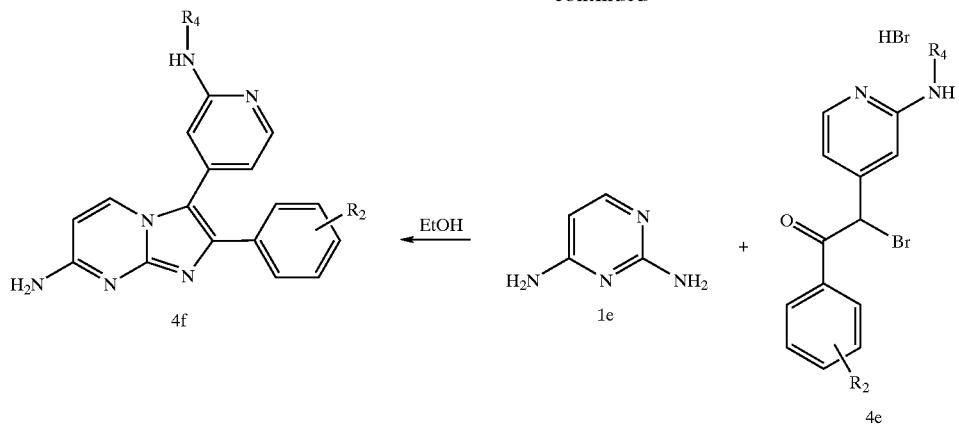

The examples below describe in greater particularity the chemical synthesis of representative compounds of the present invention. The remaining compounds disclosed herein can be prepared similarly in accordance with one or more of these methods. No attempt has been made to optimize the yields obtained in these reactions, and it would be clear to one skilled in the art that variations in reaction times, temperatures, solvents, and/or reagents could increase such yields.

EXAMPLE 1

Imidazo[1,2-a]pyrimidin-7-a mine, 3-[2-[(Phenylmethyl)amino]-4-pyridinyl]-2-[3-(trifluoromethyl)phenyl]

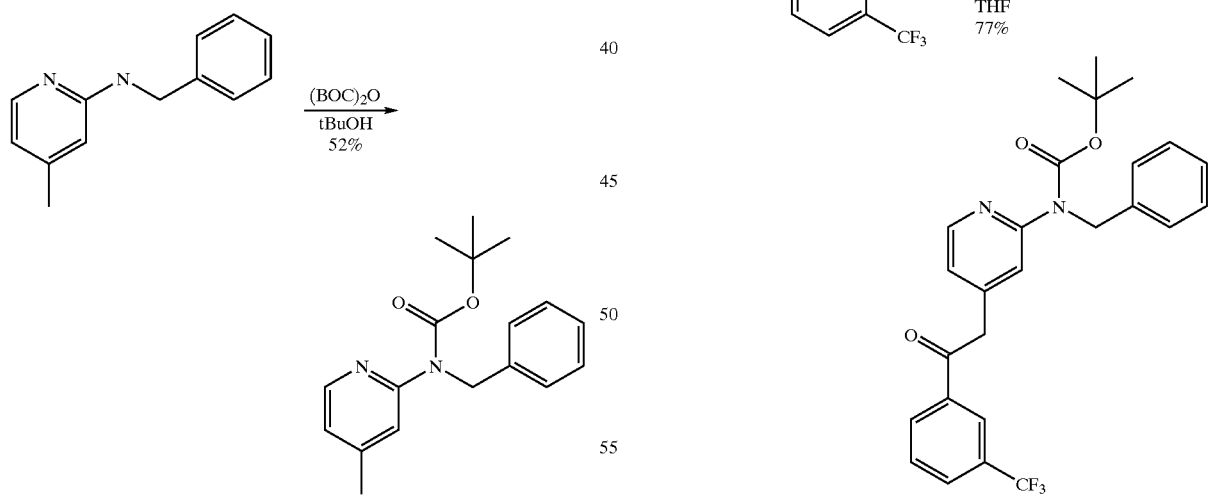

6.59 g (31.18 mmoles) of Di-t-butyidicarbonate was added to 5.44 g (27.44 mmoles) of 2-benyzlamino-4-methylpyridine in 40 ml t-butanol. After 18 hours the solvent was removed in vacuo. The residue was triturated with hexane and filtered. The filtrate was concentrated in vacuo to give 4.25 g of the protected amine. $^1$H NMR (300 MHz, DMSO-$d_6$) δ 8.22 (1H, d, J=5.1 Hz), 6.99 (1H, d, J=5.1 Hz), 5.10 (2H, s), 2.31 (3H,s), 1.38 (9H,s).

61 ml (61 mmoles) of 1.0 M Sodium bis(trimethylsilyl) amide in tetrahydrofuran was added drop-wise to a solution of 8.97 g (30.07 mmoles) of the N-Boc-2-benzylamino-4-methylpyridine and 6.58 g (30.07 mmoles) of ethyl 3-trifluoromethylbenzoate in 60 ml tetrahydrofuran by addition funnel under nitrogen atmosphere. After eighteen hours the reaction was quenched with saturated ammonium chloride solution, and the solvent removed in vacuo. The residue was extracted into 300 ml of ethyl acetate and washed 2×200 ml water, 1×100 ml brine, dried over sodium sulfate, filtered and concentrated in vacuo to give a brown oil. Column chromatography using 5:1 hexane/ethyl acetate afforded the 10.92 g of product as a thick yellow oil. $^1$H NMR (300 MHz, DMSO-$d_6$) δ 7.59 (1H, s), 5.11 (2H, s), 4.62 (2H, s), 1.33 (9H, s).

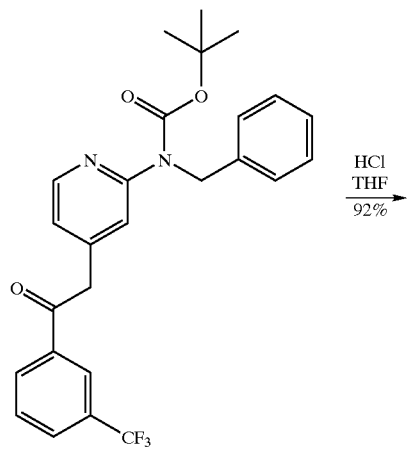

HCl
THF
92%

10.92 g (23.21 mmoles) of the protected amine was refluxed in 100 ml tetrahydrofuran containing 20 ml of 6M HCl solution for 1 hour, cooled, diluted with 220 ml water and extracted in 2×250 ml ethyl acetate. The organic layers were separated, combined, washed with 200 ml water, 2×100 ml brine, dried over magnesium sulfate, filtered, and concentrated in vacuo to give 7.91 g of a viscous red oil. MH$^+$=371.

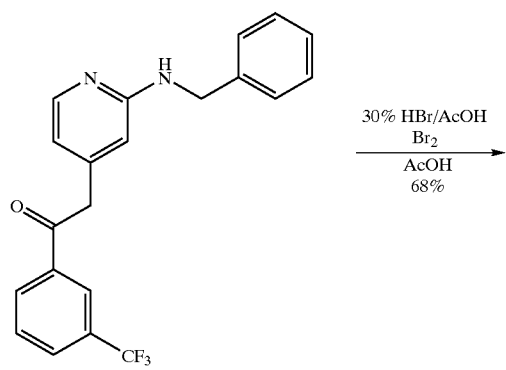

30% HBr/AcOH
Br$_2$
AcOH
68%

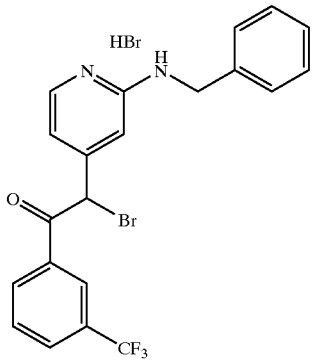

1.30 ml (6.61 mmoles) of 30% hydrogen bromide in acetic acid was added to 2.33 g (6.29 mmoles) of the ketone in 10 ml glacial acetic acid. A solution of 0.35 ml (6.79 mmoles) of bromine in 1.65 ml glacial acetic acid was added dropwise and the reaction heated to 60° C. for one hour, cooled to room temperature, and diluted with ether. The oily residue that formed was washed with ether to give 2.27 g (4.28 mmoles) of the crude bromide. MH$^+$=450.

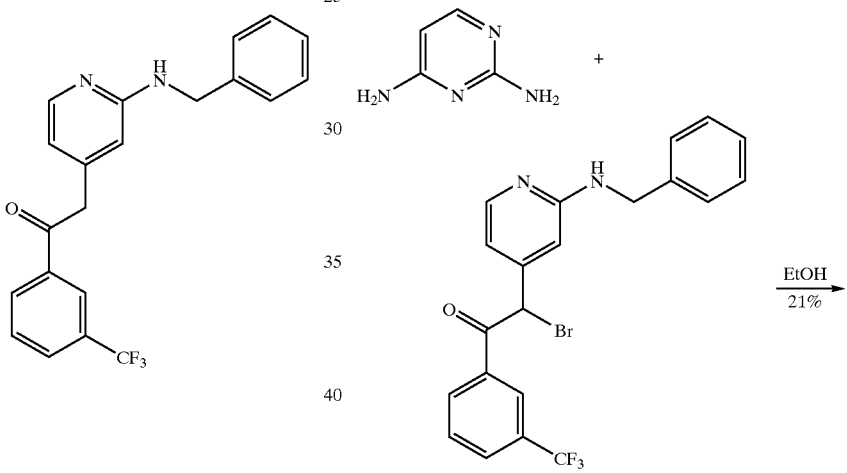

EtOH
21%

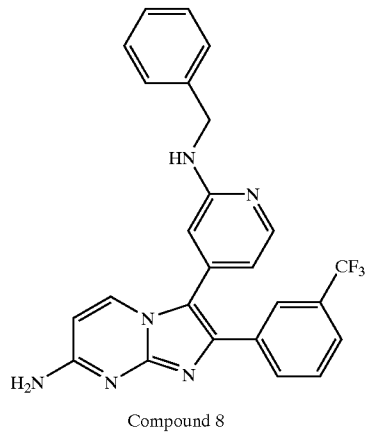

Compound 8

A solution of 1.89 g (17.13 mmoles) of 2,4-diaminopyrimidine in 20 ml ethanol was heated to 80° C. A solution of 2.27 g (4.28 mmoles) of the crude bromide in 50 ml ethanol was added drop-wise by addition funnel. The reaction was stirred at 80° C. for one hour then cooled to room temperature. Approximately one-half of the solvent was removed in vacuo. Upon cooling to room temperature the reaction was filtered. The filtrate was concentrated in vacuo, diluted with 250 ml ethyl acetate and washed 2×100 ml 0.5M sodium hydroxide solution, dried over sodium sulfate, filtered, and concentrated in vacuo to give a red-brown oil. Column chromatography using 2% methanol in ethyl acetate afforded 0.4161 g of Compound 8 (Imidazo[1,2-a]pyrimidin-7-amine, 3-[2-[(phenylmethyl)amino]-4-pyridinyl]-2-[3-(trifluoromethyl)phenyl]-) as an off-white solid. MH$^+$=461.

EXAMPLE 2

1-Phenyl-2-(4-pyridinyl)-ethanone and 1-Phenyl-2-bromo-2-(4-pyridinyl)-ethanone 1.0M Sodium bis(trimethylsilyl)amide (40 mL, 0.04 mol) in tetrahydrofuran was added drop-wise to a solution of 1.8 g (0.02 mol) of 4-picoline and 3.0 g (0.02 mol) of ethyl benzoate in 60 ml tetrahydrofuran by addition funnel under nitrogen atmosphere. After eighteen hours the reaction was quenched with saturated ammonium chloride solution, and the solvent removed in vacuo. The residue was extracted into 100 ml of ethyl acetate and washed 2×200 ml water, 1×100 ml brine, dried over sodium sulfate, filtered and concentrated in vacuo to give an oil. Trituration with ether gives 1.6 g of the product 1-phenyl-2-(4-pyridinyl)-ethanone. MH+ 198.

1.8 ml (8.9 mmoles) of 35% hydrogen bromide in acetic acid was added to 1.6 g (8.1 mmol) of the ketone in 10 ml glacial acetic acid. A solution of 0.46 ml (8.9 mmol) of bromine in 1.65 ml glacial acetic acid was added drop-wise and the reaction heated to 60° C. for one hour, cooled to room temperature, and diluted with ether. The solid that formed was washed with ether to give 2.5 g of the bromide as the HBr salt of 1-phenyl-2-bromo-2-(4-pyridinyl)-ethanone. MH$^+$=276.

EXAMPLE 3

Imidazo[1,2-a]pyrimidin-7-amine, 2-Phenyl-3-(4-pyridinyl)

A solution of 1.2 g (11 mmoles) of 2,4-diaminopyrimidine in 10 ml of ethanol was heated to 80° C. A solution of 1.0 g (2.8 mmol) of the bromide in 20 ml of ethanol was added drop-wise by addition funnel. The reaction was stirred at 80° C. for 3 hours then cooled to room temperature. Approximately one-half of the solvent was removed in vacuo. Upon cooling to room temperature the reaction was filtered. The filtrate was concentrated in vacuo, diluted with 250 ml ethyl acetate and washed with 2×100 ml 0.5M sodium hydroxide solution, dried over sodium sulfate, filtered, and concentrated in vacuo to give a red-brown oil. Trituration of the residue with EtOAc, followed by filtration gave 0.108 g of Compound 5 as an off-white solid. MH$^+$=288.

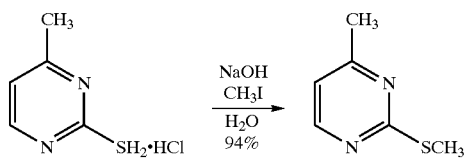

13.23 g (93.2 mmoles) of Iodomethane was added drop-wise by syringe to a solution of 13.38 g (84.73 mmoles) of 2-mercapto-4-methylpyrimidine hydrochloride and 7.46 g (186.4 mmoles) sodium hydroxide in 120 ml of water. After 2 hours the reaction was extracted with 2×125 ml dichloromethane. The organic layers were separated, combined, dried over Na$_2$SO$_4$, filtered, and concentrated in vacuo to give 11.14 g (79.45 mmoles) of 4-methyl-2-(methylthio)pyrimidine as a red oil. MH$^+$=140.9.

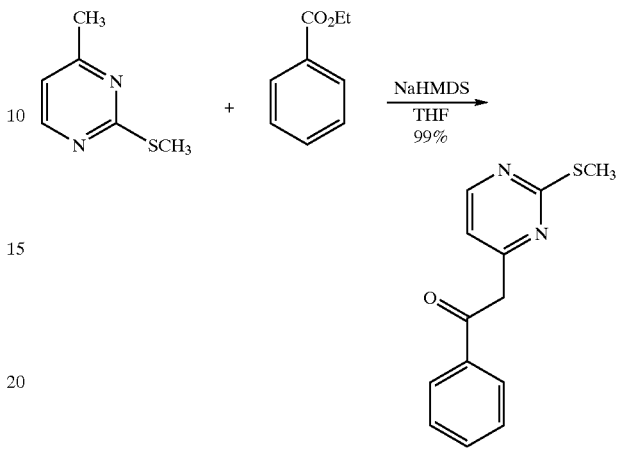

86 ml (86 mmoles) of 1.0 M sodium bis(trimethylsilyl)amide in tetrahydrofuran was added drop-wise by addition funnel to a solution of 6.03 g (43 mmoles) 4-methyl-2-(methylthio)pyrimidine and 6.46 g (43 mmoles) ethyl benzoate in 86 ml tetrahydrofuran under a nitrogen atmosphere. After 2 hours the reaction was quenched with saturated ammonium chloride solution. Most of the tetrahydrofuran was removed in vacuo. The residue was diluted with 400 ml ethyl acetate and 200 ml water. The organic layer was separated and washed 2×100 ml saturated sodium chloride solution, separated, dried over Na$_2$SO$_4$, filtered, and concentrated in vacuo to give 10.45 g (42.77 mmoles) of 2-[2-(methyl thio)pyrimidin-4-yl]-1-phenyle thanone as a viscous red-brown oil that solidified upon standing. MH$^+$=244.9.

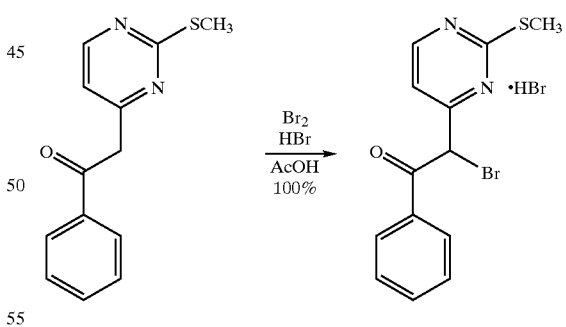

9 ml (44.91 mmoles) of 30% hydrogen bromide in acetic acid was added to 1 0.45 g (42.77 mmoles) of the ketone in 80 ml glacial acetic acid. A solution of 2.40 ml (46.19 mmoles) of bromine in 2.60 ml glacial acetic acid was added drop-wise and the reaction heated to 60° C. for 45 minutes, cooled to room temperature, and diluted with ether. The resultant slurry was filtered and washed with ether and dried in vacuo to give 18.06 g (44.69 mmolese of the crude bromide. MH$^+$=324.9.

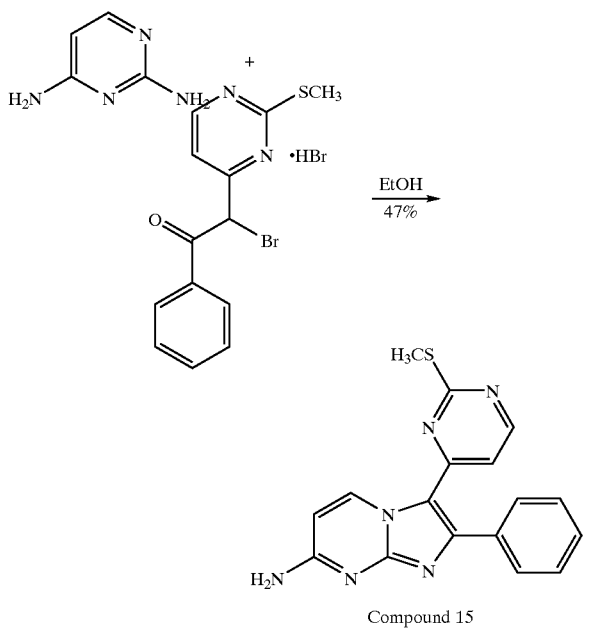

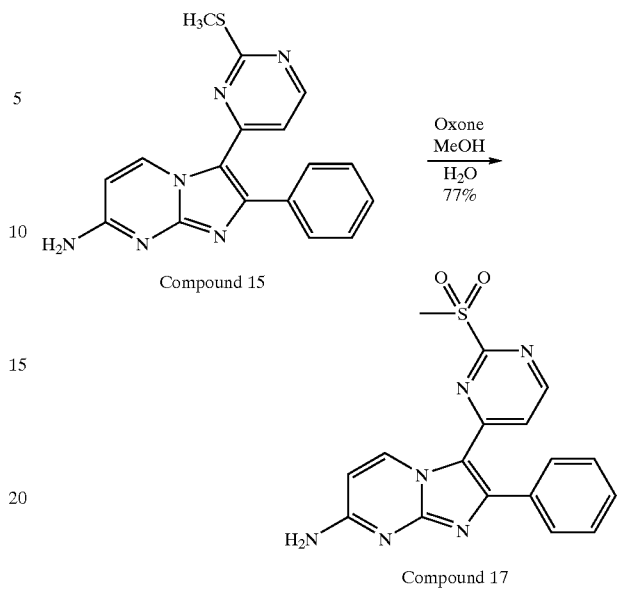

A solution of 18.83 g (171.08 mmoles) of 2,4-diaminopyrimidine in 150 ml ethanol was heated to 80° C. A solution of 18.06 g (42.77 mmoles) of the crude bromide in 350 ml ethanol was added drop-wise by addition funnel. The reaction was stirred at reflux for two hours. Upon cooling to room temperature the reaction was filtered. The precipitate was stirred in 150 ml of 0.5M sodium hydroxide solution. The precipitate was collected by filtration, washed with water, ether and hexane to give 6.72 g (21.1 mmoles) of the product as a light yellow solid. MH$^+$=334.9.

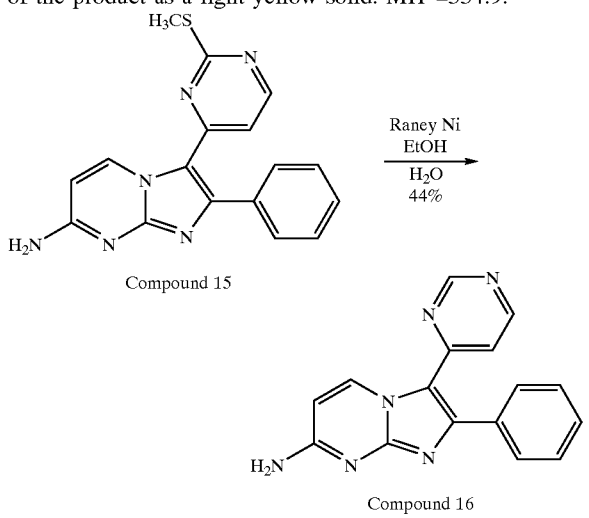

A mixture of 0.60 g (1.79 mmoles) of the thiomethylpyrimidine, approximately 4 ml of a 50% Raney Nickel in water solution, 40 ml ethanol and 20 ml water was refluxed for eighteen hours under a nitrogen atmosphere. The reaction was cooled to room temperature and filtered through celite. The celite was washed with ethanol. The combined filtrates were concentrated in vacuo. The residue was collected by trituration with ethanol, collected by filtration and washed with ether to give 0.2310 g of the pyrimidine as a yellow solid (Compound 16). MH$^+$=289.0.

A solution of 8.28 g (13.46 mmoles) of oxone in 75 ml water was added drop-wise by addition funnel to 1.50 g (4.49 mmoles) of the thiomethyl pyrimidine in 77 ml methanol. The resultant slurry was stirred at room temperature for eighteen hours, filtered, and the filtrate concentrated in vacuo to remove the methanol. The residue was diluted with 100 ml water and neutralized with solid sodium bicarbonate. The resultant slurry was filtered and the precipitate washed with water, ether, and dried to give 1.27 g (3.46 mmoles) of the methylsulfone pyrimidine as a yellow solid (Compound 17). MH$^+$=367.0.

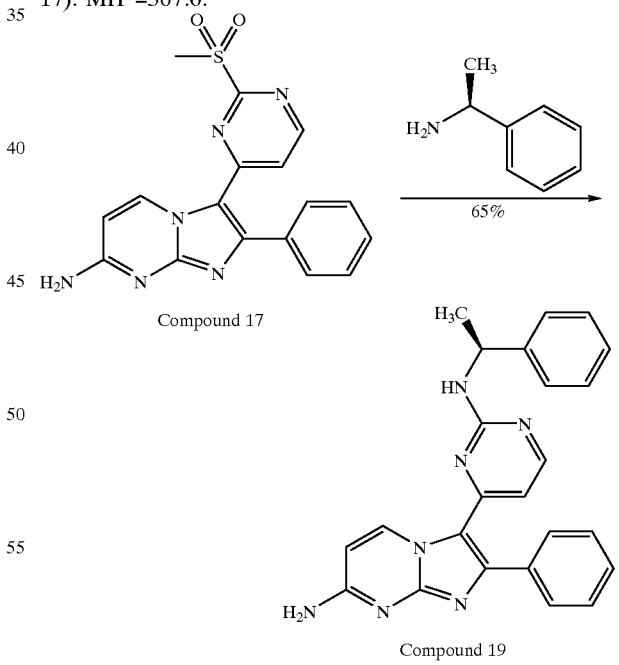

A mixture of 0.55 g (1.5 mmoles) of the methylsulfone pyrimidine and 1.82 g (15 mmoles) of (S)-(−)-α-methylbenzylamine was heated at 140° C. for 30 minutes, cooled to room temperature, diluted with 100 ml ethyl acetate and washed 3×50 ml water, 1×50 ml saturated sodium chloride solution, dried over Na$_2$SO$_4$, filtered, and concentrated in vacuo to afford a yellow oil. Column chromatography using 100% ethyl acetate as eluent afforded 0.3977 g (0.98 mmoles) of the product as a light yellow solid (Compound 19). MH+=408.1.

B. Assays

EXAMPLE 4

Assays for Inhibition of p38

The biological activities of certain compounds of the invention were demonstrated by in vitro and in vivo assays. As discussed previously, agents which inhabit the activity of the enzyme p38 inhibit the production of the inflammotory cytokines TNF-α and IL-1β.

Select compounds of the invention are listed in Table 1, which provides mass spectral data as well as data showing each compound's ability to inhibit p38 as shown by inhibition of TNF-α production. The assays by which such data was generated are described below.

TABLE 1

Compounds tested for their ability to inhibit p38 as shown by the inhibition of TNF-α production

| Compound No. | MS ci (M + 1) | LPS/PBMC $IC_{50}$ nM (TNF-α) | Mouse % Inhibition TNF-α production 10 mg/kg |
|---|---|---|---|
| 1 | 306 | 49 | 100 |
| 2 | 306 | 55 | 100 |
| 3 | 356 | 333 | 26 |
| 4 | 340 | 21 | 100 |
| 5 | 288 | 55 | 100 |
| 6 | 411 | 6 | 42 |
| 7 | 356 | 35 | 99 |
| 8 | 461 | 4 | 19 |
| 9 | 476 | 0.5 | 97 |
| 10 | 353 | 37 | 68 |
| 11 | 403 | 27 | 38 |
| 12 | 353 | 10 | 51 |
| 13 | 357 | 278 | 85 |
| 14 | 372 | 8 | 63 |
| 15 | 335 | 28 | 23 |
| 16 | 289 | 304 | 73 |
| 17 | 367 | 3414 | — |
| 18 | 435 | 520 | 10 |
| 19 | 408 | 0.40 | 100 |
| 20 | 424 | 14 | — |
| 21 | 425 | 2 | 97 |
| 22 | 432 | 1 | 74 |
| 23 | 319 | 90 | 87 |
| 24 | 307 | 199 | 91 |
| 25 | 322 | 162 | 47 |

PBMC Whole Cell Assay

Representative compounds of the present invention were tested in an in vitro whole cell assay using peripheral blood mononuclear cells ("PBMC's") which were obtained from human blood as follows. Freshly obtained venous blood was anticoagulated with heparin, diluted with an equal volume of phosphate buffered saline ("PBS") and placed in a sterile tube or other container. Aliquots (30 mL) of this mixture were transferred to centrifuge tubes which were underlaid with Ficoll-Hypaque (15 mL). The prepared tubes were centrifuged at 400×g without braking for 30 min at room temperature. Approximately ½ to ⅔ of the platelet layer above the mononuclear cell band was removed with a pipette. The majority of the mononuclear cell layer was carefully removed using a pipette and these PBMC's were diluted with PBS and spun at 600×g for 15 min. The resulting PBMC's were washed with another portion of PBS and spun at 400×g for 10 min at room temperature. The recovered pellets were diluted in low endotoxin RPMI/1% FCS culture medium and gave a cell concentration of 0.5–2.0×10⁶ PMBC/mL. A small volume of the suspension was removed for counting on a hemocytometer and the remaining preparation was centrifuged at 200×g for 15 min at room temperature. The recovered pelleted PMBC's were re-suspended in RPMI/1% FCS to a concentration of 1.67× 10⁶/mL.

To run the assay, the PBMC suspension (180 μL) was transferred to duplicate wells of a 96-well flat-bottom microtiter plate and incubated for 1 h at 37° C. A solution of test compound (10 μL, prepared at 20×the desired final concentration) was added to each well and the plate was incubated for 1 h at 37° C. A solution (10 μL) of LPS in RPMI/1% FCS (200 ng/mL) was added and the wells were incubated overnight at 37° C. The supernate (100 μL) was removed from each well and diluted with RPMI/1% FCS (400 μL). The samples were analyzed for TNF-α using a commercial ELISA kit (Genzyme). Data are shown in Table 1 above.

In Vivo Rodent Assay

The ability of the compounds of Formula I to inhibit LPS-induced TNF-α production was demonstrated in the following in vivo rodent assays. Mice (BALB/cJ females, Jackson Laboratories) were fasted for 30 min. prior to oral dosing with 5–10 mL/kg of a test compound at 5–50 mg/kg. Thirty minutes after dosing, the animals were injected intraperitoneally with LPS at 1 mg/kg and returned to their cages for 1 h. Animals were anesthetized by $CO_2$, exsanguinated by cardiac puncture and whole blood collected (0.1–0.7 mL). The blood was allowed to clot and serum was transferred to a centrifuge tube. This sample was centrifuged, and serum was collected, aliquoted, and frozen at −80° C. Samples were tested by commercial ELISA's for TNF-α (Endogen for mouse TNF-α). The % inhibition of the test compounds was calculated by the following formula: % inhibition=[1−(sample-BKG)/(CTRL-BKG)]×100. Data are shown in Table 1 above.

Recombinant p38 Assay

Compounds of the invention were measured for their ability to inhibit the activity of p38 by the following in vitro assay. A solution (38 μL) of purified recombinant p38 (where the amount of enzyme was determined empirically considering the linear range of the assay and the acceptable signal to noise ratio; 6×His-p38 expressed in *E.coli*), myelin basic protein substrate (also determined empirically), and a buffer of pH 7.5 (Hepes: 25 mM; $MgCl_2$: 10 mM; $MnCl_2$: 10 mM) were added to 92 wells of a 96-well round bottom polypropylene plate. The remaining wells were used for control ("CTRL") and background ("BKG"). The CTRL was prepared with the enzyme, substrate buffer and 21% DMSO, and the BKG was prepared with substrate buffer and 2% DMSO. A solution (12 μL) of the test compound in DMSO (compounds were diluted to 125 μM in 10% DMSO/$H_2O$ and assayed at 25 μM where the final DMSO concentration was 2%) was added to the testing wells. The ATP/³³P-ATP solution (10 μL containing 50 μM unlabeled ATP and 1 μCi ³³P-ATP) was added to all wells and the completed plates were mixed and incubated at 30° C. for 30 min. Ice-cold 50% TCA/10 mM sodium phosphate (60 μL) were added to each well and the plates were kept on ice for 15 min. The contents of each well were transferred to the wells of a 96-well filterplate (Millipore, MultiScreen-DP) and the filterplate was placed on a vacuum manifold, fitted with a waste collection tray. The wells were washed five times with 10% TCA/10 mM sodium phosphate (200 μL) under vacuum. MicroScint-20 scintillant was added, the plates were sealed using Topseal-S sheets and counted in a Packard TopCount scintillation counter using a $^{33}P$ liquid program with color quench correction, where the output is in color quench-corrected cpm. Although compounds were initially tested at 10 μM, if warranted the compounds were tested at 4-fold increments above and below that concentration. In addition, $IC_{50}$'s were calculated for some compounds using the Deltagraph 4-parameter curve-fitting program. No data are shown.

In Vitro IL-1β Assay

The ability of compounds of the invention to inhibit IL-1β production may be determined by the following in vitro assay. Plastic-adherent cells are prepared from PBMC's. Briefly, PBMC's are added to the wells of a 96-well plate as above, incubated for 1 h at 37° C., and the adherent cells prepared by gently resuspending the non-adherent cells with a pipetor, removing and discarding them and gently washing the wells 3 times with 200 μL culture medium. Additional culture medium (180 μL) is added to the wells after the final wash. Compound addition, LPS stimulation, incubation and supernate harvest are the same as for TNF-α. Supernates are assayed for interleukin-1β using a commercial ELISA (Genzyme). No data are shown.

What is claimed is:

1. A compound of Formula I,

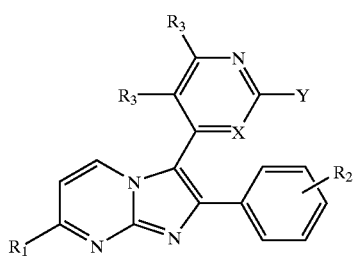

Formula I or a pharmaceutically acceptable salt thereof, wherein
   (a) $R_1$ is selected from the group consisting of $NH_2$, $C_{1-5}$alkylamino, di$C_{1-5}$alkylamino, hydroxy, $C_{1-5}$alkoxy, phenylmethylamino, heterocyclymethyl, $C_{1-5}$alkylcarbonylamino, and substituted phenylcarbonylamino, wherein
      said phenylmethylamino and heterocyclylmethyl may be substituted on its phenyl moiety by one or more members selected from the group consisting of halogen, $C_{1-5}$alkyl, $C_{1-5}$alkoxy, aryl$C_{1-3}$alkylamino, R'R"NCH=N— and OR''', the R', R" and R''' being independently selected from H, $C_{1-5}$alkyl, phenylmethyl, substituted phenylmethyl, α-alkyl-phenylmethyl, substituted α-alkyl-phenylmethyl, heterocyclylmethyl, and substituted heterocyclylmethyl;
   (b) Y is selected from the group consisting of H, halogen, heterocycle, $OR_4$, $SR_4$, $NR_4$ and $NR_4R_5$, wherein
      $R_4$ and $R_5$ are independently selected from H, heterocyclyl, $C_{3-5}$carbocycle, phenyl, α-alkyl-phenyl$C_{1-5}$alkyl, straight or branched alkyl optionally substituted with R, NR, $N(R)_2$, $C_{3-5}$carbocycle, phenyl or substituted phenyt, wherein (i) R is H, halogen, $C_{1-5}$alkyl, phenyl methyl, substituted phenyl methyl, $SO_2Ph$, pyridyl, or pyridyl methyl, and (ii) said phenyl, heterocyclyl, and α-alkyl-phenyl$C_{1-5}$alkyl may be substituted by one or more members selected from the group consisting of halogen, $C_{1-5}$alkyl, $C_{1-5}$alkoxy, aryl$C_{1-3}$alkylamino, phenyl methyl, substituted phenyl methyl, R'R"NCH=N— and OR''' as defined in (a) hereof;
   (c) $R_2$ is one to five members independently selected from the group consisting of halogen, trifluoromethyl, —$NCH_2PH$, $C_{1-5}$alkyl, and $C_{1-5}$alkoxy;
   (d) $R_3$ is H or, taken together, an aromatic ring; and
   (e) X is N or CH.

2. The compound of claim 1, wherein X is CH.
3. The compound of claim 1, wherein $R_1$ is $NH_2$.
4. The compound of claim 1, wherein Y is $NR_4$ and $R_4$ is phenylmethyl.
5. The compound of claim 1, wherein $R_2$ is a member selected from the group consisting of halogen, trifluoromethyl, —$NCH_2PH$ and $C_{1-5}$alkoxy.
6. The compound of claim 1, wherein Y is selected from the group consisting of

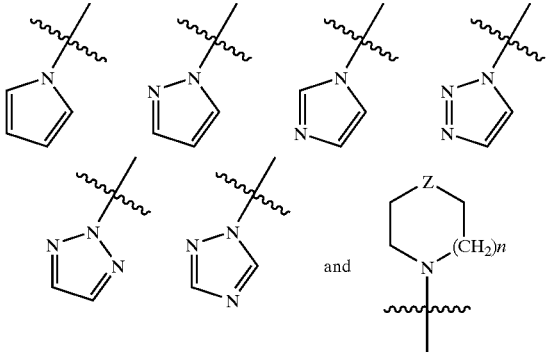

wherein Z is —$CH_2$—, —$O_2S$—, —O—, —N(R)—, —OS—, or S; R is H, halogen, $C_{1-5}$alkyl, phenylmethyl, substituted phenylmethyl, $SO_2Ph$, pyridyl, or pyridylmethyl; and n is 0–5.

7. The compound of claim 1 wherein $R_4$ is selected from

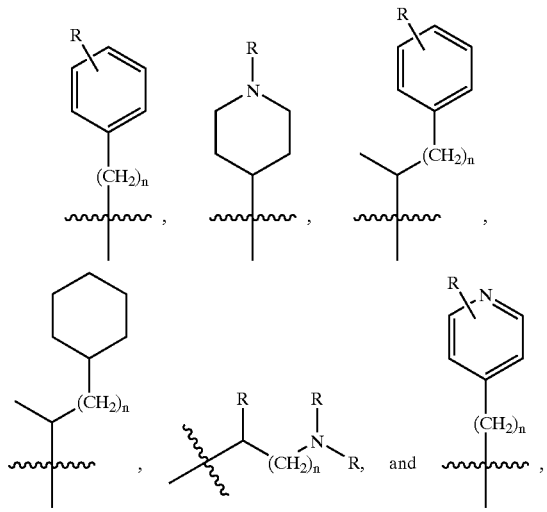

wherein each R can be the same as or different and is independently selected from H, halogen, $C_{1-5}$alkyl, phenylmethyl, substituted phenylmethyl, $SO_2Ph$, pyridyl and pyridylmethyl, and n is 0–5.

8. The compound of claim 1 which is 2-(3-chloro-4-fluorophenyl)-3-(4-pyridinyl)-imidazo[1,2-a]pyrimidin-7-amine.

9. The compound of claim 1 which is 2-phenyl-3-(4-pyridinyl)-imidazo[1,2-a]pyrimidin-7-amine.

10. The compound of claim 1 which is 2-(4-fluorophenyl)-3-[2-[(phenylmethyl)amino]4-pyridinyl]-imidazo[1,2-a]pyrimidin-7-amine.

11. The compound of claim 1 which is 3-(4-pyridinyl)-2-[3-(trifluoromethyl)phenyl]-imidazo[1,2-a]pyrimidin-7-amine.

12. The compound of claim 1 which is 3-[2-[(phenylmethyl)amino]4-pyridinyl]-2-[3-(trifluoromethyl)phenyl]-imidazo[1,2-a]pyrimidin-7-amine.

13. The compound of claim 1 which is 2-(4-fluorophenyl)-3-(4-quinolinyl)-imidazo[1,2-a]pyrimidin-7-amine.

14. The compound of claim 1 which is 2-(3-chlorophenyl)-3-(4-pyridinyl)imidazo[1,2-a]pyrimidin-7-amine.

15. The compound of claim 1 which is 2-(4-fluorophenyl)-3-[2-(methylthio)-4-pyrimidinyl]imidazo[1,2-a]pyrimidin-7-amine.

16. The compound of claim 1 which is 3-[2-(methylthio)-4-pyrimidinyl]-2-[3-(trifluoromethyl)phenyl]imidazo[1,2-a]pyrimidin-7-amine.

17. The compound of claim 1 which is 2-(3-fluorophenyl)-3-[2-(methylthio)-4-pyrimidinyl]imidazo[1,2-a]pyrimidin-7-amine.

18. The compound of claim 1 which is 3-(4-pyridinyl)-2-[3-(trifluoromethyl)phenyl]imidazo[1,2-a]pyrimidin-7-amine.

19. The compound of claim 1 which is 3-[2-(methylthio)-4-pyrimidinyl]-2-phenylimidazo[1,2-a]pyrimidin-7-amine.

20. The compound of claim 1 which is 2-phenyl-3-(4-pyridinyl)imidazo[1,2-a]pyrimidin-7-amine.

21. The compound of claim 1 which is 3-[2-(methylsulfonyl)-4-pyrimidinyl]-2-phenylimidazo[1,2-a]pyrimidin-7-amine.

22. The compound of claim 1 which is 3-[2-(methylsulfonyl)-4-pyrimidinyl]-2-[3-(trifluoromethyl)phenyl]imidazo[1,2-a]pyrimidin-7-amine.

23. The compound of claim 1 which is 2-phenyl-3-[2-[[(1s)-1-phenylethyl]amino]-4-pyrimidinyl]imidazo[1,2-a]pyrimidin-7-amine.

24. The compound of claim 1 which is 3-[[[(4-methoxyphenyl)methyl]amino]-4-pyrimidinyl]-2-phenylimidazo[1,2-a]pyrimidin-7-amine.

25. The compound of claim 1 which is 3-(2-methoxy4-pyrimidinyl)-2-phenylimidazo[1,2-a]pyrimidin-7-amine.

26. The compound of claim 1 which is 2-(4-fluorophenyl)-3-(4-pyrimidinyl)imidazo[1,2-a]pyrimidin-7-amine.

27. The compound of claim 1 which is 2-(3-fluorophenyl)-3-(4-pyridinyl)-imidazo[1,2-a]pyrimidin-7-amine.

28. The compound of claim 1 which is 2-(4-fluorophenyl)-3-(4-pyridinyl)-imidazo[1,2-a]pyrimidin-7-amine.

29. The compound of claim 1 which is 3-[2-[[(1S)-1-phenylethyl]amino]-4-pyrimidinyl]-2-[3-(trifluoromethyl)phenyl]imidazo[1,2-a]pyrimidin-7-amine.

30. The compound of claim 1 which is 2-phenyl-3-[2-(1-piperidinyl)4-pyrimidinyl]imidazo[1,2-a]pyrimidin-7-amine.

31. The compound of claim 1 which is 3-[2-[[(1S)-1-cyclohexylethyl]amino]-4-pyrimidinyl]-2-(4-fluorophenyl)imidazo[1,2-a]pyrimidin-7-amine.

32. The compound of claim 1 which is 2-(4-Fluorophenyl)-3-[3-[[(1S)1-phenylethyl]amino]-4-pyridinyl]imidazo[1,2-a]pyrimidin-7-amine.

33. The compound of claim 1 which is 3-(2-Bromo-4-pyridinyl)-2-(4-fluorophenyl)imidazo[1,2-a]pyrimidin-7-amine.

34. The compound of claim 1 which is 3-(2-Bromo-4-pyridinyl)2-[3-(trifluoromethyl)phenyl]imidazo[1,2-a]pyrimidin-7-amine.

35. A pharmaceutical composition comprising the compound of claim 1 and a pharmaceutically acceptable carrier.

36. A method of treating a subject suffering from rheumatoid arthritis, which method comprises administering to the subject a therapeutically effective dose of the compound of claim 1.

* * * * *

UNITED STATES PATENT AND TRADEMARK OFFICE
CERTIFICATE OF CORRECTION

PATENT NO.   : 6,610,697 B1
DATED        : August 26, 2003
INVENTOR(S)  : John H. Dodd, James R. Henry and Kenneth C. Rupert It is certified that error appears in the above-identified patent and that said Letters Patent is hereby corrected as shown below:

<u>Column 32,</u>
Line 4, should read -- The compound of claim 1 which is 3-(2-methoxy-4-pyrimidinyl) -- (dash is to be inserted after "methoxy")

Signed and Sealed this

Seventh Day of September, 2004

JON W. DUDAS
*Director of the United States Patent and Trademark Office*